United States Patent
Xiao et al.

(10) Patent No.: US 9,434,767 B2
(45) Date of Patent: Sep. 6, 2016

(54) METHOD FOR PREPARING ATOSIBAN ACETATE

(75) Inventors: Qing Xiao, Guangdong (CN); Jian Liu, Guangdong (CN); Hongling Li, Guangdong (CN); Yaping Ma, Guangdong (CN); Jiancheng Yuan, Guangdong (CN)

(73) Assignee: HYBIO PHARMACEUTICAL CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 13/579,030

(22) PCT Filed: Dec. 22, 2011

(86) PCT No.: PCT/CN2011/084414
§ 371 (c)(1), (2), (4) Date: Aug. 14, 2012

(87) PCT Pub. No.: WO2012/083861
PCT Pub. Date: Jun. 28, 2012

(65) Prior Publication Data
US 2013/0261285 A1    Oct. 3, 2013

(30) Foreign Application Priority Data
Dec. 24, 2010  (CN) .......................... 2010 1 0604790

(51) Int. Cl.
*C07K 7/64* (2006.01)
*C07K 7/16* (2006.01)

(52) U.S. Cl.
CPC .. *C07K 7/64* (2013.01); *C07K 7/16* (2013.01)

(58) Field of Classification Search
None
See application file for complete search history.

(56) References Cited

U.S. PATENT DOCUMENTS

| | | | |
|---|---|---|---|
| 4,504,469 A * | 3/1985 | Melin et al. | 514/11.6 |
| 2006/0276626 A1* | 12/2006 | Tovi et al. | 530/328 |
| 2013/0261285 A1* | 10/2013 | Xiao et al. | 530/315 |

FOREIGN PATENT DOCUMENTS

| CN | 102127146 A | * | 7/2011 |
|---|---|---|---|
| IN | 2004MU00284 A | * | 7/2006 |
| IN | 2010MU01265 A | * | 10/2010 |
| WO | WO 2006119388 A2 | * | 11/2006 |

* cited by examiner

*Primary Examiner* — Maury Audet
(74) *Attorney, Agent, or Firm* — PROI Intellectual Property US

(57) ABSTRACT

The present invention provides a method for preparing atosiban acetate. The method comprises the following steps of: synthesizing to obtain linear atosiban; dissolving the linear atosiban in an acetonitrile aqueous solution, adjusting the pH value with ammonia water, adding $H_2O_2$ for oxidizing, filtering, purifying, and transferring salt to obtain the atosiban acetate. In the present invention, an appropriate route is provided, the linear atosiban is synthesized by adopting a solid phase method, and the atosiban is obtained by liquid phase oxidation. The method has the advantages of capabilities of solving the problem of insolubility of the linear atosiban, reducing the reaction size to the maximum extent and shortening reaction time, and being high in yield and easy to industrialize.

2 Claims, No Drawings

METHOD FOR PREPARING ATOSIBAN ACETATE

FIELD OF THE INVENTION

The present invention relates to a method for preparing a polypeptide drug, and in particular to a method for preparing atosiban acetate.

BACKGROUND OF THE INVENTION

Atosiban is a nonapeptide which contains three non-natural amino acids: D-Tyr(Et), Mpa and Orn, and a pair of disulfide bonds looped between Mpa and Cys, the structural formula is:

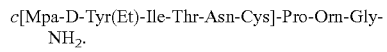

c[Mpa-D-Tyr(Et)-Ile-Thr-Asn-Cys]-Pro-Orn-Gly-NH$_2$.

By means of competing for oxytocin receptor with oxytocin, Atosiban can inhibit the combination between oxytocin and oxytocin receptor, and directly prevent the oxytocin from acting on uterus, and then inhibit the uterine contraction; as another hand, atosiban can also inhibit the hydrolysis of phosphatidylinositol and then block the generation of messenger and activity of $Ca^{2+}$, with the decreasing of activity from oxytocin, the contraction of uterine is indirectly inhabited.

At present, there are many reports about synthesis process method in China and abroad A report in China shows that the inventor found a simple process by adopting solid phase oxidation, resulting in a low purity crude product, with low yield and low application value. The aforementioned reports about atosiban synthesis process reveal that most of them adopt the method using Boc solid phase synthetic and cleaving peptide with liquid ammonia, then oxidating with liquid phase oxidation, and purifying. Those respective processes result in "the three wastes" and are too complex for industrial production. See U.S. Pat. No. 4,504,469.

SUMMARY OF THE INVENTION

The present invention provides a proper route by which the atosiban is obtained by using synthesized linear atosiban and by liquid phase oxidation. The method solves the problem of insolubility, reduces the reaction size extent and shortens reaction time to the maximum, and also the yield is high and easy to industrialize.

In order to achieve the above goal, the present invention adopts the following technical schemes:

A method for preparing atosiban acetate includes the following steps of:

synthesizing to obtain linear atosiban;

dissolving the linear atosiban in an acetonitrile aqueous solution, adjusting the pH value with ammonia water, adding $H_2O_2$ for oxidizing, filtering, purifying, and transferring to acetate salt and obtain the atosiban acetate.

The "obtaining by synthesizing" refers to obtaining the linear atosiban by the means of liquid phase synthesis method or solid phase synthesis method. Preferably, the solid phase synthesis method is more optimized, it is initiated by Fmoc-Gly-OH and amino resin with suitable substitutability, then synthesized the linear atosiban-resin by coupling one by one; then the linear atosiban is obtained through the process of cleaving the linear atosiban-resin with lysate mixture of TFA and $H_2O$ and precipitating, wherein the amino resin is preferably Rink amide resin, the substitutability of which is preferably 0.4 mmol/g to 1.0 mmol/g. The coupling agent used in the solid phase synthesis method includes DIC/HOBt, PyBOP/HOBt, HATU/HOBt or HBTU/HOBt, preferably DIC/HOBt. It is found that the coupling agent of the present invention can improve the reaction rate obviously, at the same time, the DIC/HOBt coupling system greatly reduces the production cost. The "/" means "and". The cleavage of the linear atosiban-resin is achieved by cleaving the linear atosiban-resin using the lysate mixture with the volume ratio of TFA:$H_2O$=95:5. The dosage of cleaving agent is 10-15 ml/g for linear atosiban-resin.

Linear peptide oxidization can adopt liquid phase oxidization or solid phase oxidization. As to the traditional liquid phase reaction, the liquid volume is too large, and it is difficult to operate and also takes a long time. In comparison, the solid phase oxidization generally adopts iodine oxidation, and it is convenient to operate, but easy to produce "the three wastes".

The present invention adopts the liquid phase oxidization taking $H_2O_2$ as an oxidant, which directly simplifies the production process, reduces the reaction size and oxidization time to the maximum extent.

The atosiban acetate is prepared by dissolving the linear atosiban in the acetonitrile aqueous solution, adjusting the pH value with ammonia water, adding $H_2O_2$ for oxidizing, filtering, purifying, transferring salt, and freeze-drying.

The acetonitrile aqueous solution is used for liquid phase oxidization, the volume ratio of acetonitrile is 5% to 15%, preferably 10%. The linear atosiban is insoluble in water, the reaction volume is big when the water is used as solvent, the acetonitrile aqueous solution adopted by the present invention greatly improves the solubility of linear atosiban, and reduces the reaction volume by half.

The concentration of linear atosiban in the liquid phase oxidization is 0.01 g/ml to 0.03 g/ml, preferably 0.02 g/ml. The concentration of linear atosiban directly influences the generation of multimer during oxidization, when the concentration of less than 0.01 g/ml, it brings inconvenience for industrial operation; and when the concentration is more than 0.03 g/ml, polymerization occurred between peptide molecules is less likely to filter.

The liquid phase oxidization adopts $H_2O_2$ as oxidant, the mole number of $H_2O_2$ and linear atosiban is 2-8, i.e. the amount of oxidant $H_2O_2$ is 2-8 times to the mole number of linear atosiban, preferably 5 times. Experiments show that suitable amount of $H_2O_2$ can speed up the oxidization rate and reduce the generation of polymer.

The liquid phase oxidization adopts $H_2O_2$ as oxidant, the reaction time is 5 min to 60 min in between, preferably 30 min. Experiments show that, when the oxidization time is less than 5 min, a large number of linear peptides are not oxidized to cyclopeptide, when the oxidization time is more than 60 min, multiple of linear peptides forms a cycle to for polymer. The oxidization time of the present invention is preferably 30 min, and the purity is above 85%.

The liquid phase oxidization adopts $H_2O_2$ as oxidant, the reaction temperature is 10-40 degrees Celsius, preferably 25° C. Experiments show that, when the reaction temperature is lower than 10° C., the oxidization reaction yield is below 50%, when the reaction temperature is more than 40° C., it is found that amino acid easily suffers from racemization to generate impurity that is difficult to separate. The oxidization temperature of the present invention is preferably 25° C., which not only reduces the acemization of the amino acid, but also improves the oxidization yield and reaction rate.

The liquid phase oxidization adopts 30% ammonia water to adjust the pH, in which the pH value is 8-9.

After liquid phase oxidization, the atosiban acetate is prepared by filtering with diatomite and filter membrane ordinally, purifying filtrate by preparative RP-HPLC (column C18 or C8), transferring salt, and freeze-drying.

In the present invention, the linear atosiban is oxidized by liquid phase method with $H_2O_2$, which avoids complicated operation caused by traditional liquid phase oxidization, and improves the oxidization yield by 20%-30%. The process of the present invention has the features of simple reaction, less material input, low cost, high yield or the like, and greatly reduces the generation of insolubles, the synthesis yield of the reaction can reach to 68%, with considerable economical and practical value.

The abbreviations involved in the present invention have the following meanings:
Fmoc-: Fluorenylmethoxycarbonyl
Gly: Glycine
Orn: Ornithine
Pro: Proline,
Cys: Cysteine
Asn: Asparagine
Thr: Threonine
Ile: Isoleucine
Tyr: Tyrosine
Mpa: Mercaptopropionic Acid
Boc: Tert-butoxycarbonyl
Trt: Triphenylmethyl
tBu: Tert-butyl
Et: Ethyl
HOBt: 1-Hydroxybenzotriazole
DIC: Diisopropylcarbodiimide
TFA: Trifluoroacetic acid
PyBOP: Benzotriazole-1-yl-oxytripyrrolidinophosphonium hexafluorophosphate
HBTU: o-Benzotriazol-1-yl-N,N,N',N'-tetramethyluronium hexafluorophosphate
$H_2O_2$: hydrogen peroxide
DMF: N,N-dimethyl formamide
DCM: Dichloromethane

DETAILED DESCRIPTION OF THE PREFERRED EMBODIMENTS

Example 1

Preparing the Linear Atosiban Peptide Resin (i) 6.25 g of Rink Amide resin (substitutability=0.8 mmol/g) is put into a reaction bottle, DMF is added into the bottle and washed twice, then swelled for 30 min with DMF. Fmoc protecting group of Rink Amide resin is removed with 30-40 ml of 20% DBLK, washed for 4 times with DMF, then washed twice with DCM after removal, the product is detected by ninhydrin detecting method, the resin is reddish-brown.

(ii) 4.46 g of Fmoc-Gly-OH and 2.43 g of HOBt dissolved in a suitable amount of DMF, which had been pre-activated with 3.05 ml DIC; the mixture is, added to the reaction bottle, and reacted for 2 h, the resin is negative by ninhydrin detecting method, after the reaction, the product is washed for 4 times with DMF, then washed twice with DCM, if the resin is positive, repeating the above condensation reaction until negative.

(iii) Fmoc-Orn(Boc)-OH, Fmoc-Pro-OH, Fmoc-Cys(Trt)-OH, Fmoc-Asn(Trt)-OH, Fmoc-Thr(tBu)-OH, Fmoc-Ile-OH, Fmoc-D-Tyr(ET)-OH and Mpa(Trt)-OH are coupled orderly.

Example 2

Cleaving the Linear Atosiban Peptide Resin 5.15 g of linear atosiban is prepared by washing the linear atosiban peptide resin obtained from Example 1 for 3 times with 30 ml of methanol, adding the dry resin obtained to 150 ml of mixed solution with a volume ratio of $TFA:H_2O=95:5$, reacting for 2 hours at 25° C. and filtering, washing the resin for 3 times with few trifluoroacetic acid, combining the filtrate and pouring into 1500 ml glacial ether, making rest for 2 hours, centrifugally separating the linear atosiban, washing for 3 times, and drying in a vacuum drier, MS: 995.3, HPLC: 91.5%, content: 65.5%, synthesis yield: 68%.

Example 3

Oxidizing the Linear Atosiban 2.85 g of atosiban acetate is prepared by dissolving the linear atosiban obtained from Example 2 in 250 ml of 5% acetonitrile aqueous solution, adjusting the pH value to 8 to 9 with 30% ammonia water, adding 0.60 g of $H_2O_2$, reacting for 10 min at 25° C., monitoring with HPLC (HPLC: 75.6%), filtering after reaction, purifying filtrate by preparative RP-HPLC (column C18 or C8), transferring salt, and freeze-drying, MS: 994.5, HPLC: 99.4%.

Example 4

Oxidizing the Linear Atosiban 3.01 g of atosiban acetate is prepared by dissolving the linear atosiban obtained from Example 2 in 250 ml of 10% acetonitrile aqueous solution, adjusting the pH value to 8 to 9 with 30% ammonia water, adding 0.85 g of $H_2O_2$, reacting for 30 min at 25° C., monitoring with HPLC (HPLC: 89.5%), filtering after reaction, purifying filtrate by preparative RP-HPLC (column C18 or C8), transferring salt, and freeze-drying, MS: 994.5, HPLC: 99.6%.

Example 5

Oxidizing the Linear Atosiban 2.95 g of atosiban acetate is prepared by dissolving the linear atosiban obtained from Example 2 in 250 ml of 10% acetonitrile aqueous solution, adjusting the pH value to 8 to 9 with 30% ammonia water, adding 0.85 g of $H_2O_2$, reacting for 60 min at 25° C., monitoring with HPLC (HPLC: 83.5%), filtering after reaction, purifying filtrate by preparative RP-HPLC (column C18 or C8), transferring salt, and freeze-drying, MS: 994.5, HPLC: 99.4%.

The above is the further detailed description of the invention in conjunction with specific preferred examples, but it should not be considered that the specific examples of the invention are only limited to the these descriptions. For one of ordinary skill in the art, many deductions and replacements can be made without departing from the inventive concept. Such deductions and replacements should fall within the scope of protection of the invention.

What is claimed is:

1. A method for preparing atosiban acetate, comprising the following steps of:
   1) synthesizing linear atosiban by solid-phase synthesis method using Rink amide resin with a coupling agent, wherein the coupling agent can be chosen from DIC/HOBt, yBOP/HOBt, HATU/HOBt or HBTU/HOBt; and
   2) dissolving the linear atosiban with 5-15% acetonitrile aqueous solution, wherein the molar ratio of linear atosiban to $H_2O_2$ is 1:2-8, concentration of linear atosiban is 0.01-0.03 g/ml, through the following steps:
      a) adjusting the pH to 8-9 with ammonia water,
      b) oxidizing with $H_2O_2$, during oxidizing with $H_2O_2$ the oxidizing time is 5-60 min and the oxidizing reaction temperature is 10-40° C.,
      c) filtering through diatomite to obtain crude filtrate and micro-filtering through microporous filter membrane to obtain micro-filtrate,
      d) purifying by RP-HPLC, and
      e) transferring salt to obtain the atosiban acetate.

2. The preparation method according to claim 1, wherein the filtering is ordinally and further comprising freeze-drying the obtained atosiban acetate.

* * * * *